US011229559B2

United States Patent
Sakaguchi et al.

(10) Patent No.: US 11,229,559 B2
(45) Date of Patent: Jan. 25, 2022

(54) ABSORBENT ARTICLE

(71) Applicant: UNICHARM CORPORATION, Ehime (JP)

(72) Inventors: Satoru Sakaguchi, Kagawa (JP); Maika Takahashi, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 482 days.

(21) Appl. No.: 16/095,699

(22) PCT Filed: Jan. 13, 2017

(86) PCT No.: PCT/JP2017/001073
§ 371 (c)(1),
(2) Date: Oct. 23, 2018

(87) PCT Pub. No.: WO2017/195401
PCT Pub. Date: Nov. 16, 2017

(65) Prior Publication Data
US 2019/0142652 A1    May 16, 2019

(30) Foreign Application Priority Data

May 10, 2016   (JP) .............................. JP2016-094942

(51) Int. Cl.
*A61F 13/15*   (2006.01)
*A61F 13/49*   (2006.01)
(Continued)

(52) U.S. Cl.
CPC .. *A61F 13/49011* (2013.01); *A61F 13/00063* (2013.01); *A61F 13/15617* (2013.01);
(Continued)

(58) Field of Classification Search
CPC ............ A61F 13/49011; A61F 13/0063; A61F 13/15617; A61F 13/49014;
(Continued)

(56) References Cited

U.S. PATENT DOCUMENTS

2004/0260261 A1   12/2004 Yoshida et al.
2011/0208142 A1    8/2011 Roe et al.
(Continued)

FOREIGN PATENT DOCUMENTS

CN    104768509 A    7/2015
JP    2007-530232 A   11/2007
(Continued)

*Primary Examiner* — Jacqueline F Stephens
(74) *Attorney, Agent, or Firm* — Hauptman Ham, LLP

(57) ABSTRACT

An absorbent article has front and back surface sheets, and an absorbent body disposed within the front surface sheet and back surface sheet laminate. The absorbent article is further provided with a stretchable waist member disposed within the laminate in a manner enabling stretching in the width direction, and a pair of stretchable side members formed on the peripheral edge of the laminate in a manner enabling stretching in the width direction. One member and the other member of the pair of stretchable side members are formed, respectively, on one end and the other end of the laminate in the width direction. The stretchable waist member overlaps with each of the pair of stretchable side members in the lengthwise direction, is disposed further on the non-skin side than the absorbent body in the thickness direction, and overlaps with the absorbent body in the thickness direction but is not joined thereto.

5 Claims, 4 Drawing Sheets

(51) Int. Cl.
  *A61F 13/00*  (2006.01)
  *A61F 13/494* (2006.01)
  *A61F 13/56*  (2006.01)

(52) U.S. Cl.
  CPC .. *A61F 13/49014* (2013.01); *A61F 13/49015* (2013.01); *A61F 13/49413* (2013.01); *A61F 13/5633* (2013.01); *A61F 2013/4905* (2013.01); *A61F 2013/49057* (2013.01); *A61F 2013/49093* (2013.01)

(58) Field of Classification Search
  CPC .......... A61F 13/49015; A61F 13/49413; A61F 13/5633; A61F 2013/4905; A61F 2013/49057; A61F 2013/49093
  See application file for complete search history.

(56) References Cited

U.S. PATENT DOCUMENTS

| | | |
|---|---|---|
| 2014/0025030 A1 | 1/2014 | Kline et al. |
| 2014/0074055 A1* | 3/2014 | Roe .................. A61F 13/49011 604/385.01 |
| 2015/0216737 A1 | 8/2015 | Tsang et al. |
| 2015/0290048 A1 | 10/2015 | Sugiyama et al. |

FOREIGN PATENT DOCUMENTS

| | | |
|---|---|---|
| JP | 2013-74974 A | 4/2013 |
| JP | 2013-146611 A | 8/2013 |
| JP | 2014-83235 A | 5/2014 |
| JP | 2014-87383 A | 5/2014 |
| JP | 2014-138906 A | 7/2014 |
| JP | 2015-37591 A | 2/2015 |
| WO | 2005/097028 A1 | 10/2005 |
| WO | 2009/082290 A1 | 7/2009 |

* cited by examiner

FIG. 3A
FIG. 3B
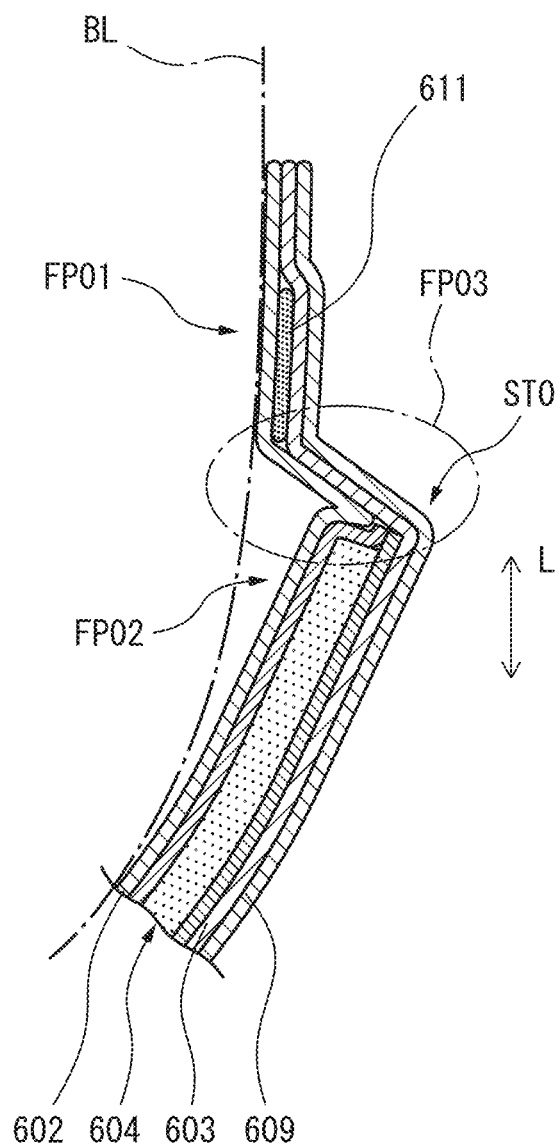
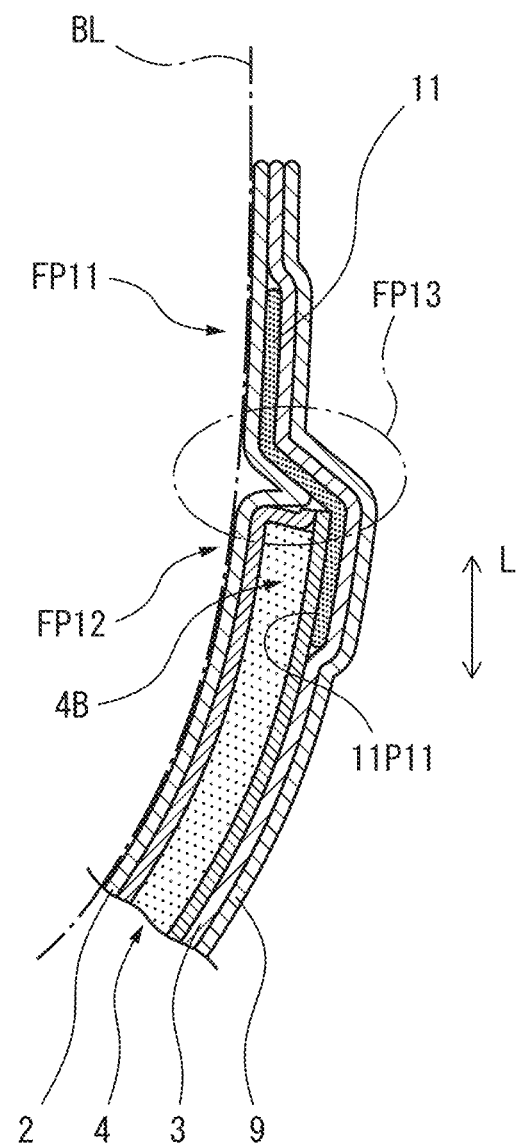

ABSORBENT ARTICLE

RELATED APPLICATIONS

The present application is a National Phase of International Application Number PCT/JP2017/001073, filed on Jan. 13, 2017, and claims priority to Japanese Application No. 2016-094942, filed on May 10, 2016.

FIELD

The present invention relates to an absorbent article.

BACKGROUND

Absorbent articles such as disposable diapers are known. In order to increase fitting onto the human body when worn, in such absorbent articles there are formed expandable-and-shrinkable members that are expandable and shrinkable in the widthwise direction of the absorbent articles. Examples of such expandable-and-shrinkable members include a waist expandable-and-shrinkable member formed along the widthwise direction on the back side of the girth portion of a disposable diaper, and a pair of side expandable-and-shrinkable members formed on both ends in the widthwise direction of a disposable diaper.

As absorbent articles comprising such expandable-and-shrinkable members, Patent Literature 1 and Patent Literature 2 disclose disposable absorbent articles and disposable diapers. The disposable absorbent article of Patent Literature 1 comprises an elastomer element (corresponding to a waist expandable-and-shrinkable member) situated along the widthwise direction on the back side of the girth portion, without overlapping or being bonded to the absorbent body in the thickness direction, and a pair of tab sections (corresponding to side expandable-and-shrinkable members) situated on both ends in the widthwise direction. Also, the disposable diaper of Patent Literature 2 comprises a sheet-like elastic component (corresponding to a waist expandable-and-shrinkable member) situated along the widthwise direction on the back side of the girth portion, partially overlapping and bonded to an absorbent body in the thickness direction.

CITATION LIST

Patent Literature

[PTL 1] Japanese Patent Public Inspection No. 2007-530232
[PTL 2] Japanese Unexamined Patent Publication No. 2013-146611

DISCLOSURE OF INVENTION

Technical Problem

In an absorbent article, incidentally, a waist expandable-and-shrinkable member is disposed between a front sheet and a back sheet. In the disposable absorbent article of Patent Literature 1, the elastomer element, or waist expandable-and-shrinkable member, is disposed between a front sheet and a back sheet, both sides thereof being bonded to the front sheet and back sheet, respectively. However, the waist expandable-and-shrinkable member is not overlapping with an absorbent body in the thickness direction, and is therefore not bonded to the absorbent body. In other words, in the laminate of the front sheet and the back sheet, the waist expandable-and-shrinkable member and the absorbent body are disposed apart from each other in the lengthwise direction. When the waist expandable-and-shrinkable member and the absorbent body are thus disposed apart from each other in the lengthwise direction, even if the waist expandable-and-shrinkable member shrinks and approaches a tighter fit with the back side of the wearer, the absorbent body cannot shrink since it has no expandability and shrinkability, and it cannot follow movement of the waist expandable-and-shrinkable member since it is disposed apart from the waist expandable-and-shrinkable member, and therefore it can potentially become separated from the back side of the wearer. That is, a level difference can potentially be formed between the waist expandable-and-shrinkable member and the absorbent body on the back side of the wearer. When such a level difference is formed, it reduces the practical compatibility with the body and lowers the degree of wear comfort of the absorbent article, and this can result in insufficient absorption of excreted fluid by the portion of the absorbent body on the back side of the wearer.

In order to minimize formation of such a level difference there has been devised a method of overlapping the portion of the absorbent body on the back side of the wearer with the waist expandable-and-shrinkable member, and bonding it with adhesive, as with the disposable diaper of Patent Literature 2, for example. Since the waist expandable-and-shrinkable member and the absorbent body are bonded in this case, the absorbent body can follow movement of the waist expandable-and-shrinkable member. When the waist expandable-and-shrinkable member shrinks, however, the absorbent body also shrinks and deforms in shape, such that the absorption performance of the absorbent body is lowered at the absorbent body portion on the back side of the wearer, or the wear comfort of the absorbent body can potentially be reduced by formation of wrinkles and the like.

It is an object of the present invention to provide an absorbent article that is highly compatible with the body when worn, and that can also minimize reduction in absorption performance of the absorbent body and reduction in wear comfort.

Solution to Problem

The absorbent article of the present invention is as follows.

(1) An absorbent article comprising a front sheet, a back sheet and an absorbent body disposed in a laminate of the front sheet and the back sheet, and having a lengthwise direction, a widthwise direction and a thickness direction, the absorbent article comprising a waist expandable-and-shrinkable member that is expandable and shrinkable in an expansion-and-shrink direction and disposed in the laminate so that the expansion-and-shrink direction is along the widthwise direction; and a pair of side expandable-and-shrinkable members that are expandable and shrinkable in the expansion-and-shrink direction, the pair of side expandable-and-shrinkable members being formed on a perimeter section of the laminate so that the expansion-and-shrink direction is along the widthwise direction, and one and the other of the pair of side expandable-and-shrinkable members being formed on one edge and the other edge, respectively, in the widthwise direction of the laminate, wherein the waist expandable-and-shrinkable member overlaps with each of the pair of side expandable-and-shrinkable members in the lengthwise direction, is disposed on a non-skin side with respect to the absorbent body in the thickness direction, and overlaps but non-bonded to the absorbent body in the thickness direction.

By having the aforementioned configuration that employs a waist expandable-and-shrinkable member and a pair of side expandable-and-shrinkable members, the absorbent article can have increased compatibility with the body when worn, while also minimizing reduction in absorption performance or reduction in wear comfort of the absorbent body. Specifically, it is as follows.

The waist expandable-and-shrinkable member and the absorbent body are overlapping in the thickness direction but are non-bonded, or in other words, they are not bonded with adhesive, and therefore the waist expandable-and-shrinkable member and absorbent body can move relative to each other. Consequently, even when the waist expandable-and-shrinkable member has shrunk in the widthwise direction so as to increase compatibility with the body when worn, the absorbent body is virtually unshrunk and thus the absorbent body undergoes virtually none of the deformation accompanying shrink, thereby making it possible to minimize reduction in absorption performance of the absorbent body and reduction in wear comfort of the absorbent body. Furthermore, as the waist expandable-and-shrinkable member positioned on the non-skin side shrinks while the absorbent body positioned on the skin side undergoes virtually no shrink, pressure is exerted by the waist expandable-and-shrinkable member toward the skin side, i.e. toward the absorbent body side, and the absorbent body can be pressed against the skin side. This allows the absorbent body to come into close contact with the wearer, so that the absorption performance can be improved while increasing compatibility with the body when worn. However, when the absorbent body is pressed against the skin side in this way, mainly the center section in the widthwise direction of the absorbent body is pressed against the skin side of the wearer, but the edges in the widthwise direction of the absorbent body can potentially tend to be separated from the skin side. Nevertheless, since the force of shrink of the pair of side expandable-and-shrinkable members acts on both ends in the widthwise direction of the laminate of the front sheet and the back sheet, the laminate, and particularly the back sheet, is pulled to the pair of side expandable-and-shrinkable members, whereby the edges in the widthwise direction of the absorbent body become pressed against the skin side by the back sheet and the edges in the widthwise direction of the absorbent body no longer separate from the skin side. This allows the function of the waist expandable-and-shrinkable member pressing the absorbent body onto the skin side, to apply over the entire widthwise direction of the absorbent body.

The absorbent article of the present invention may also be (2) the absorbent article according to (1) above, wherein the waist expandable-and-shrinkable member and each of the pair of side expandable-and-shrinkable members are disposed apart from each other in the widthwise direction.

Since the waist expandable-and-shrinkable member and each of the pair of side expandable-and-shrinkable members is disposed apart from each other in the widthwise direction in this absorbent article, the portions of the laminate without expansion and shrink between the waist expandable-and-shrinkable member and each of the pair of side expandable-and-shrinkable members pull both ends of the laminate in the widthwise direction without expanding, the absorbent body can be more strongly pressed on the skin side. This allows the absorbent body to come into close contact with the wearer, so that the absorption performance can be improved while increasing compatibility with the body when worn.

The absorbent article of the present invention may also be (3) the absorbent article according to (1) or (2) above, wherein one direction in the lengthwise direction is a frontward direction and the other is a backward direction, and in the lengthwise direction, an edge of the absorbent body in the backward direction is situated between an edge in the frontward direction and an edge in the backward direction of the waist expandable-and-shrinkable member.

In this absorbent article, the waist expandable-and-shrinkable member and the absorbent body are shifted in the lengthwise direction, or in other words, the waist expandable-and-shrinkable member is shifted more toward the backward direction in the lengthwise direction than the absorbent body. Consequently, compared to when the waist expandable-and-shrinkable member is completely overlapping with the absorbent body in the lengthwise direction, friction and the like between the waist expandable-and-shrinkable member and the absorbent body is reduced and it becomes easier to expand the waist expandable-and-shrinkable member in the widthwise direction. This allows the waist expandable-and-shrinkable member to apply firmer pressure on the absorbent body side, and to press the absorbent body more to the skin side. This allows the absorbent body to come into close contact with the wearer, so that the absorption performance can be improved while increasing compatibility with the body when worn.

The absorbent article of the present invention may also be (4) the absorbent article according to any one of (1) to (3) above, wherein each of the pair of side expandable-and-shrinkable members comprises fastening tape on an outer side in the widthwise direction, and the fastening tape overlaps with the waist expandable-and-shrinkable member in the lengthwise direction.

In this absorbent article, the fastening tape overlaps with the waist expandable-and-shrinkable member in the lengthwise direction. Consequently, when the pair of side expandable-and-shrinkable members are expanded and the fastening tape of each side expandable-and-shrinkable member has been fastened to the target tape, the force of shrink of the side expandable-and-shrinkable members and the force of shrink of the waist expandable-and-shrinkable member are coordinated between the fastening tapes, allowing the absorbent body to be more firmly pressed against the skin side. This allows the absorbent body to come into close contact with the wearer, so that the absorption performance can be improved while increasing compatibility with the body when worn.

The absorbent article of the present invention may also be (5) the absorbent article according to any one of (1) to (4) above, wherein each of the pair of side expandable-and-shrinkable members overlaps with the absorbent body in the lengthwise direction.

In this absorbent article, each of the pair of side expandable-and-shrinkable members overlaps with the absorbent body in the lengthwise direction, and therefore the force of shrink of each of the pair of side expandable-and-shrinkable members is more easily transmitted to the absorbent body, and the absorbent body can be more greatly pressed against the skin side. This allows the absorbent body to come into close contact with the wearer, so that the absorption performance can be improved while increasing compatibility with the body when worn.

Advantageous Effects of Invention

According to the present invention, it is possible to provide an absorbent article that is highly compatible with the body when worn, and that can also minimize reduction in absorption performance of the absorbent body and reduction in wear comfort.

BRIEF DESCRIPTION OF DRAWINGS

FIGS. 3A and 3B is a schematic view illustrating the function of the absorbent article according to the embodiment.

DESCRIPTION OF EMBODIMENTS

An absorbent article according to an embodiment will now be explained with reference to the attached drawings, using a tape-like (open type) disposable diaper as an example. However, the types and uses of the absorbent article of the present invention are not limited to this example, and the present invention may be applied to other absorbent articles such as pants-type disposable diapers, for example, without departing from a scope of the subject matter of the present invention.

Figure 1:
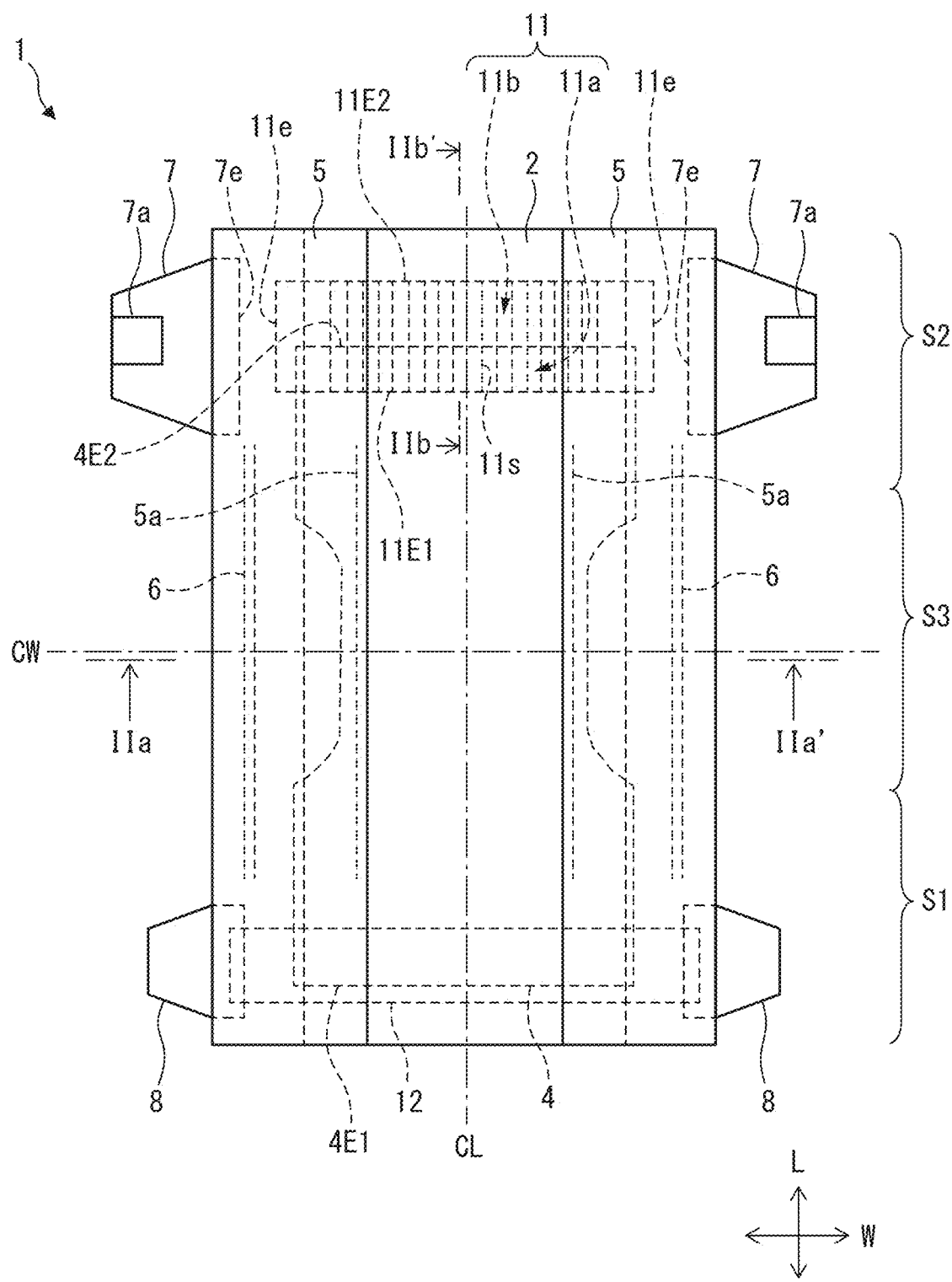
FIG. 1 is a diagram showing an absorbent article according to an embodiment.
Figure 2A:
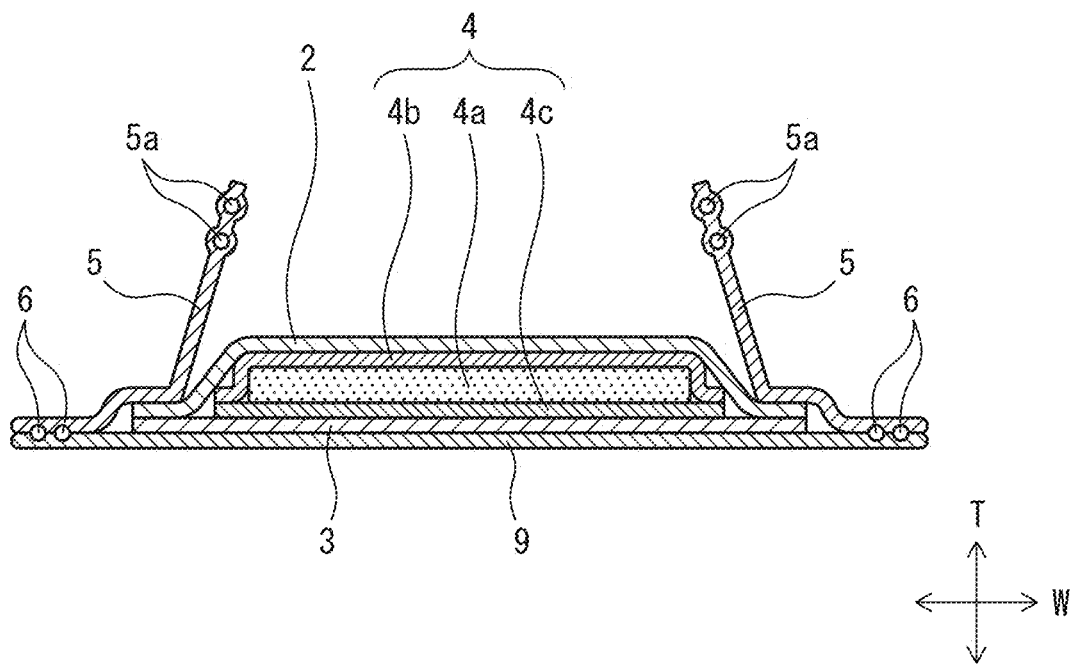
FIGS. 2A and 2B are diagrams showing the absorbent article according to the embodiment.
Figure 2B:
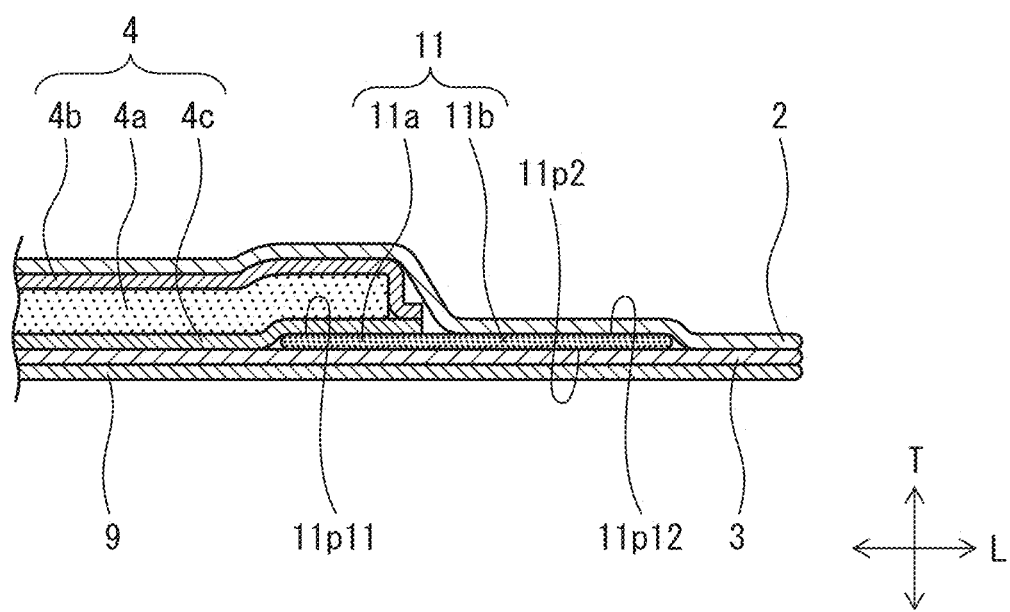

FIG. 1, FIGS. 2A and 2B are diagrams showing an absorbent article 1 (disposable diaper), and specifically, FIG. 1 shows a plan view of the absorbent article 1 in the deployed, spread-out state, FIG. 2A is a cross-sectional view along line IIa-IIa' of FIG. 1, and FIG. 2B is a cross-sectional view along line IIb-IIb' of FIG. 1. The absorbent article 1 has a lengthwise direction L, a widthwise direction W perpendicular to the lengthwise direction L, and a thickness direction T perpendicular to the lengthwise direction L and the widthwise direction W, and also has a center axis line CL extending through the center of the widthwise direction W and extending in the lengthwise direction L, and a center axis line CW extending through the center of the lengthwise direction L and extending in the widthwise direction W.

The absorbent article 1 also has, in the lengthwise direction L, a back girth region S2 corresponding to the girth around the back side of the wearer, an abdominal girth region S1 corresponding to the girth around the abdominal side of the wearer, and a crotch region S3 located between the back girth region S2 and the abdominal girth region S1, corresponding to the crotch of the wearer. The absorbent article 1 is worn as a diaper, for example, by connecting each fastening tape (described below) at both ends in the widthwise direction W of the back girth region S2 and a to-be-bonded member (described below) at the center section in the widthwise direction W of the abdominal girth region S1. The crotch region S3 may be narrowed in the widthwise direction W. The direction toward the back girth region S2 and the direction toward the abdominal girth region S1 in the lengthwise direction L are referred to as the "backward direction" and "frontward direction", respectively.

Throughout the present description, unless otherwise specified, the simple phrase "as planar view" will be used to mean that the absorbent article 1 in the deployed spread-out flat state is viewed from the upper side in the thickness direction. The terms "skin side" and "non-skin side" refer, respectively, to the side relatively near the skin side and the side relatively away from the skin side of the wearer, in the thickness direction of the absorbent article, when the wearer of the absorbent article has worn the absorbent article. Also, the direction toward the center axis line CL is the direction on the inner side in the widthwise direction W, and the direction receding from the center axis line CL is the direction on the outer side in the widthwise direction W. The direction toward the center axis line CW is the direction on the inner side in the lengthwise direction L, and the direction receding from the center axis line CW is the direction on the outer side in the lengthwise direction L.

The absorbent article 1 comprises a front sheet 2, a back sheet 3 and an absorbent body 4. However, the lengthwise direction, widthwise direction and thickness direction of the front sheet 2, back sheet 3 and absorbent body 4 all match the lengthwise direction L, widthwise direction W and thickness direction T of the absorbent article 1. Thus, the lengthwise direction L, widthwise direction W and thickness direction T are each used for the lengthwise direction, widthwise direction and thickness direction for the front sheet 2, back sheet 3 and absorbent body 4 as well, and the skin side and non-skin side are respectively used for the side relatively near and the side relatively away from the skin side of the wearer, in the thickness direction.

The front sheet 2 is a liquid-permeable sheet situated on the skin side of the wearer. The front sheet 2 may be any liquid-permeable sheet, such as, for example, a liquid-permeable nonwoven fabric or woven fabric, a liquid-permeable hole-formed synthetic resin film, a composite sheet thereof, or the like. The back sheet 3 is a liquid-impermeable sheet situated on the non-skin side of the wearer. The back sheet 3 may be any liquid-impermeable sheet, such as, for example, a liquid-impermeable nonwoven fabric or synthetic resin film, a composite sheet thereof, an SMS nonwoven fabric, or the like. The absorbent body 4 is a liquid-absorbing and liquid-retaining material situated inside the laminate of the front sheet 2 and the back sheet 3 (hereunder also referred to simply as "laminate"), i.e. between the front sheet 2 and the back sheet 3, and for this embodiment, it includes an absorbent body core 4a and core wraps 4b, 4c that subsume the absorbent body core 4a. The absorbent body 4 may be pulp fiber, synthetic fiber, an absorbing polymer or the like. The absorbent body 4 and each of the front sheet 2 and back sheet 3 are bonded with adhesive, the front sheet 2 and back sheet 3 being bonded with adhesive at their peripheries. The adhesive used for bonding between the front sheet 2, absorbent body 4 and back sheet 3 may be a known material that is commonly used in absorbent articles 1, such as a thermoplastic adhesive.

The absorbent article 1 further comprises a pair of leak resistant walls 5, 5, leg expandable-and-shrinkable members 6, 6 and an outer sheet 9. The pair of leak resistant walls 5, 5 are a pair of side section sheets that extend along the lengthwise direction L so as to cover the surface of both sides in the widthwise direction W of the front sheet 2, and they are disposed across a distance in the widthwise direction W. The pair of leak resistant walls 5, 5 have fixed ends at their edges on the outer sides in the widthwise direction W fixed on the surface of both sides in the widthwise direction W of the front sheet 2, and have free ends forming gather sections that are expandable and shrinkable at their edges on the inner side in the widthwise direction W. Near each of the free ends of the pair of leak resistant walls 5, 5, there are situated two linear elastic solids 5a such as rubber, for example, extending along the lengthwise direction L. The leg expandable-and-shrinkable member 6 is an elastic material such as rubber that expands and shrinks in the lengthwise direction L of each of both sides in the widthwise direction W of the crotch region S3 that contacts with the femoral region of the wearer. The outer sheet 9 reinforces the back sheet 3 on the non-skin side of the back sheet 3, improving the hand feel, and being mutually connected to the perimeter sections of the pair of leak resistant walls 5, 5 while bonded to the non-skin side of the back sheet 3. There are no particular restrictions on the materials for the leak resistant walls 5 and the outer sheet 9, and examples include the material for the front sheet 2, for the leak resistant walls 5, and the material for the back sheet 3, for the outer sheet 9.

The absorbent article 1 further comprises a waist expandable-and-shrinkable member 11 and a pair of side expandable-and-shrinkable members 7, 7, in the back girth region S2.

The waist expandable-and-shrinkable member 11 is an expandable-and-shrinkable sheet that is expandable and shrinkable in the expansion-and-shrink direction, and it is disposed in the laminate so that its expansion-and-shrink direction extends along the widthwise direction W. The waist expandable-and-shrinkable member 11 functions as a waist gather that is expandable and shrinkable in the widthwise direction W, for example. For this embodiment, the waist expandable-and-shrinkable member 11 extends in the widthwise direction W. This can increase compatibility with the body, and especially the back side, when it is worn. The material of the waist expandable-and-shrinkable member 11 is not particularly restricted so long as it is expandable and shrinkable, and it may be expandable and shrinkable as a material, or expandable and shrinkable in shape, or expandable and shrinkable by combination with an elastic member. Examples for the material of the waist expandable-and-shrinkable member 11 include a film expandable-and-shrinkable member such as a polyurethane film or polystyrene film, a sheet-like expandable-and-shrinkable member that is a combination of styrene-based rubber, olefin-based rubber, urethane-based rubber or the like with a nonwoven fabric, a paper or the like, or, an expandable-and-shrinkable nonwoven fabric. Instead of an expandable-and-shrinkable sheet it may be an expandable-and-shrinkable member in the form of a rubber thread.

The waist expandable-and-shrinkable member 11 is situated between the absorbent body 4 and front sheet 2 in the thickness direction T, and at least a portion thereof overlaps with the absorbent body 4. For this embodiment, a portion of the waist expandable-and-shrinkable member 11 overlaps and contacts with the absorbent body 4 in the thickness direction T. In other words, in the lengthwise direction L as planar view, an edge 4E2 in the backward direction of the absorbent body 4 is situated between an edge 11E1 in the frontward direction and an edge 11E2 in the backward direction of the waist expandable-and-shrinkable member 11, and is in mutual contact therewith. Thus it may be said that, in the lengthwise direction L as planar view, the waist expandable-and-shrinkable member 11 is shifted more toward the backward direction in the lengthwise direction L than the absorbent body 4. This allows the waist expandable-and-shrinkable member 11 to be more easily expanded and shrunk in the widthwise direction W, compared to when the waist expandable-and-shrinkable member 11 completely overlaps and contacts with the absorbent body 4 in the lengthwise direction L as planar view.

For this embodiment, the waist expandable-and-shrinkable member 11 includes a front end portion 11a and a back end portion 11b. The front end portion 11a is the portion at the front end in the lengthwise direction L, and it overlaps and contacts with the absorbent body 4 in the thickness direction T (except for both ends in the widthwise direction W), being located on the non-skin side with respect to the absorbent body 4. On the other hand, the back end portion 11b is the portion at the back end in the lengthwise direction L, and it overlaps and contacts with the front sheet 2 without overlapping with the absorbent body 4, in the thickness direction T. With the waist expandable-and-shrinkable member 11, the skin side surface 11p11 of the front end portion 11a is in contact with the absorbent body 4, but it is non-bonded, being not bonded to the absorbent body 4, and therefore it is not adhered with adhesive, for example. On the other hand, the skin side surface 11p12 of the back end portion 11b is not in contact with the absorbent body 4, but is in contact with the front sheet 2 and is bonded to the front sheet 2, and it is therefore adhered with adhesive, for example. Also, the non-skin side surface 11p2 of the front end portion 11a and the back end portion 11b are in contact with the back sheet 3, and are bonded to the back sheet 3, and are therefore adhered with adhesive, for example. Thus, the waist expandable-and-shrinkable member 11 and the absorbent body 4 are overlapping in the thickness direction T but both are non-bonded, or in other words, they are not bonded with adhesive. Therefore, the waist expandable-and-shrinkable member 11 and the absorbent body 4 can move relative to each other. As regards both ends in the widthwise direction W of the front end portion 11a (the portions not overlapping with the absorbent body 4 in the thickness direction T), the skin side surfaces are in contact with the front sheet 2 and are bonded to the front sheet 2, while the non-skin side surfaces are in contact with the back sheet 3 and are bonded to the back sheet 3.

The pair of side expandable-and-shrinkable members 7, 7 are each an expandable-and-shrinkable sheet that is expandable and shrinkable in the expansion-and-shrink direction, and are formed at the perimeter sections of the laminate so that their expansion-and-shrink directions extend along the widthwise direction W. One and the other of the pair of side expandable-and-shrinkable members 7, 7 are formed on the one edge and the other edge, respectively, in the widthwise direction W of the laminate. The pair of side expandable-and-shrinkable members 7, 7 function, for example, as expandable-and-shrinkable side flaps for connection of the back girth region S2 to the abdominal girth region S1 during wear. Moreover, since they have expandability and shrinkability in the widthwise direction W, it is possible to expand both ends in the widthwise direction W of the laminate, and to press the absorbent body 4 in the laminate against the skin side.

Each of the pair of side expandable-and-shrinkable members 7, 7 overlaps with the absorbent body 4 in the lengthwise direction L. For this embodiment, portions of each of the pair of side expandable-and-shrinkable members 7, 7 overlap with the absorbent body 4 in the lengthwise direction L. This allows the force of shrink of each of the pair of side expandable-and-shrinkable members 7, 7 to be more easily transmitted to the absorbent body 4, and the absorbent body 4 can be more greatly pressed against the skin side. The materials of each of the pair of side expandable-and-shrinkable members 7, 7 are not particularly restricted so long as they are expandable and shrinkable, and they may be expandable and shrinkable as materials, or expandable and shrinkable in shape, or expandable and shrinkable by combination with an elastic member. The materials used for each of the pair of side expandable-and-shrinkable members 7, 7 may be, for example, the same as for the waist expandable-and-shrinkable member 11.

Each of the pair of side expandable-and-shrinkable members 7, 7 are disposed so as to protrude toward both outer sides in the widthwise direction W of the back girth region S2, and are attached with adhesive at any location on the surface of the skin side of the front sheet 2 (or leak resistant wall 5), on the surface of the non-skin side of the back sheet 3 (or outer sheet 9), and between the front sheet 2 (or leak resistant wall 5) and the back sheet 3 (or outer sheet 9) in the back girth region S2. However, each of the pair of side expandable-and-shrinkable members 7, 7 may also be formed at the extended sections of either or both the front sheet 2 (or leak resistant wall 5) and the back sheet 3 (or outer sheet 9). For this embodiment, each of the pair of side expandable-and-shrinkable members 7, 7 are disposed between the leak resistant wall 5 and the outer sheet 9, with separate members from the front sheet 2, leak resistant wall 5, back sheet 3 and outer sheet 9.

Each of the pair of side expandable-and-shrinkable members 7, 7 comprises fastening tape 7a for connection with a to-be-bonded member 12 (described below) in the abdominal girth region S1 when worn. For this embodiment, the entire to-be-bonded member 12 overlaps with the waist expandable-and-shrinkable member 11 in the lengthwise direction L. Consequently, when the pair of side expandable-and-shrinkable members 7, 7 are expanded and the fastening tape 7a of each expandable-and-shrinkable member 7 is fastened to the to-be-bonded member 12, the force of shrink of the side expandable-and-shrinkable members 7 and the force of shrink of the waist expandable-and-shrinkable member 11 are coordinated between both ends of the to-be-bonded member 12, allowing the absorbent body to be more firmly pressed against the skin side.

The waist expandable-and-shrinkable member 11 is disposed between the pair of side expandable-and-shrinkable members 7, 7. That is, it is disposed so that the waist expandable-and-shrinkable member 11 and the pair of side expandable-and-shrinkable members 7, 7 overlap in at least sections in the lengthwise direction L. Stated differently, projection onto the center axis line CL of the edge line 11e along the lengthwise direction L on the outer side in the widthwise direction W of the waist expandable-and-shrinkable member 11, and projection onto the center axis line CL of the edge line 7e along the lengthwise direction L on the inner side in the widthwise direction W of each of the pair of side expandable-and-shrinkable members 7, 7, overlap at least partially. This can improve the fitting property of the absorbent article 1 in the back girth region S2 during wear. Also, the waist expandable-and-shrinkable member 11 and each of the pair of side expandable-and-shrinkable members 7, 7 may be disposed apart from each other in the widthwise direction W, or they may be partially overlapping. For this embodiment, the waist expandable-and-shrinkable member 11 and each of the pair of side expandable-and-shrinkable members 7, 7 are disposed apart from each other in the widthwise direction W. Therefore, since the un-expandable portions of the laminate between the waist expandable-and-shrinkable member 11 and each of the pair of side expandable-and-shrinkable members 7, 7 pull both ends of the laminate in the widthwise direction W without expanding, the absorbent body 4 can be more strongly pressed against the skin side.

For this embodiment, each of the pair of side expandable-and-shrinkable members 7, 7 has higher elongation stress per unit length than the waist expandable-and-shrinkable member 11. The elongation stress of the expandable-and-shrinkable members such as the waist expandable-and-shrinkable member 11 and the side expandable-and-shrinkable member 7 were measured in the following manner, for example.

(1) The material including the expandable-and-shrinkable member was cut out as a sample, so as to include the entire expandable-and-shrinkable member in the widthwise direction W. Specifically, for the absorbent article 1 of this embodiment, a sample was cut out to a 13 mm width (corresponding to the lengthwise direction of the diaper)× 100 mm length (corresponding to the widthwise direction of the diaper), with the material including the waist expandable-and-shrinkable member 11 or the side expandable-and-shrinkable member 7 in a state of expanding to an extent that the gather disappeared. When the length in the expanded state was shorter than 100 mm, incidentally, the material was cut to 13 mm width×maximum cuttable length (corresponding to the widthwise direction of the diaper) as a sample. The cut sample in the same expanded state was marked on the inner side at 10 mm from each of both ends in the lengthwise direction. For measurement of the elongation stress, a tensile tester by Instron, Japan Co., Ltd. (for example, model 5564) or an autograph by Shimadzu Corp. (for example, model AGS-1kNG) was used.

(2) The sample of (1) above was sandwiched by an upper chuck and a lower chuck, so that the marked sections at both ends constituted the inner side edges of the upper chuck and the lower chuck, respectively. The length dimension of the sample between the chucks was 80 mm. When the length of the expandable-and-shrinkable member was shorter than 100 mm, incidentally, a length of 20 mm shorter than the shortest length among the expandable-and-shrinkable member lengths that work as a gather, was set as the length of the sample between the chucks. In order to avoid initial load of the tension of the sample, the initial chuck distance was set to be shorter than the length of the shrunk sample (the natural length). The sample was then pulled in the upper-and-lower direction at a speed of 100 mm/min so that the chucks separated from each other, thereby expanding the sample.

(3) The length dimension of the sample between the chucks, when expanded without sagging of the material sandwiching the expandable-and-shrinkable member, was 100%, and the sample was expanded until the length dimension of the sample between the chucks reached 90%, measuring the stress during expanding of the sample at that time, and recording the value at that time as the elongation stress of the expandable-and-shrinkable member. That is, for this embodiment, when the 100% length dimension of the sample was 80 mm, for example, the elongation stress during expanding to the 90% value of 72 mm was measured.

The absorbent article 1 further comprises a to-be-bonded member 12 and a pair of protrusion sections 8 in the abdominal girth region S1. The to-be-bonded member 12 is a sheet that is to be bonded to the fastening tapes 7a of the pair of side expandable-and-shrinkable members 7, 7, and when the fastening tapes 7a are hooks of hook-and-loop fasteners, for example, the to-be-bonded member 12 is a loop of a hook-and-loop fastener, and when the fastening tapes 7a are adhesive tapes, the to-be-bonded member 12 is a sheet capable of pressure-sensitive adhesion with the adhesive tape. The to-be-bonded member 12 is attached with adhesive, for example, at a location on the surface on the non-skin side of the outer sheet 9 in the abdominal girth region S1. The to-be-bonded member 12 is also disposed either partially overlapping or without any overlapping with the absorbent body 4, as planar view. For this embodiment, the to-be-bonded member 12 is disposed on the surface on the non-skin side of the outer sheet 9, so that a portion on the inner side in the lengthwise direction L of the to-be-bonded member 12 overlaps with the absorbent body 4, as planar view. This allows the absorbent body 4 to also be pressed against the skin side on the abdominal side. The pair of protrusion sections 8, 8 are sheets for connection of the abdominal girth region S1 to the back girth region S2 during wear, and they function as side flaps. The pair of protrusion sections 8 are disposed so as to protrude toward both outer sides in the widthwise direction W of the abdominal girth region S1, and are attached with adhesive at any location on the surface of the skin side of the front sheet 2 (or leak resistant wall 5), on the surface of the non-skin side of the back sheet 3 (or outer sheet 9), or between the front sheet 2 (or leak resistant wall 5) and the back sheet 3 (or outer sheet 9) in the abdominal girth region S1. However, the pair of protrusion sections 8, 8 may also be formed as the extended sections of at least one of the front sheet 2 (or leak resistant wall 5) and the back sheet 3 (or outer sheet 9). For this embodiment, the protrusion sections 8 are disposed between the leak resistant wall 5 and the outer sheet 9, as the separate members from the front sheet 2, leak resistant wall 5, back sheet 3 and outer sheet 9. The material for the protrusion sections 8 is not particularly restricted, and may be the material of the front sheet 2 or back sheet 3, for example. The protrusion sections 8 may also be absent.

An example of the function of the absorbent article 1 will now be described. FIGS. 3A and 3B are schematic views illustrating an example of the function of the absorbent article 1. In the technology of Patent Literature 1, as shown in FIG. 3A, the waist expandable-and-shrinkable member 611 of the absorbent article is disposed between a front sheet 602 and a back sheet 603, and is not overlapping with the absorbent body 604 in the thickness direction and is thus not bonded to the absorbent body 604. In other words, in the laminate of the front sheet 602 and the back sheet 603, the waist expandable-and-shrinkable member 611 and the absorbent body 604 are disposed apart from each other in the lengthwise direction L. In this case, when the waist expandable-and-shrinkable member 611 shrinks and approaches to come into close contact with the back side BL of the wearer, the portion FP01 of the front sheet 602 corresponding to the waist expandable-and-shrinkable member 611 can be in close contact with the back side BL of the wearer.

However, since the absorbent body 604 has no expandability or shrinkability and does not shrink, and is disposed apart from the waist expandable-and-shrinkable member 611, it cannot follow the movement of the waist expandable-and-shrinkable member 611, and therefore it instead separates from the back side BL of the wearer. Consequently, the portion FP02 of the front sheet 602 corresponding to the absorbent body 604 separates from the back side BL of the wearer. In addition, the front sheet 602 and back sheet 603 between the absorbent body 604 and waist expandable-and-shrinkable member 611 also have no expandability nor shrinkability and therefore do not shrink, and are not overlapping or bonded to the waist expandable-and-shrinkable member 611 in the thickness direction, such that they cannot follow movement of the waist expandable-and-shrinkable member 611, and as a result they separate from the back side BL of the wearer. Consequently, the portion FP03 of the front sheet 602 between the absorbent body 604 and the waist expandable-and-shrinkable member 611 also separates from the back side BL of the wearer. As a result, a level difference ST0 is formed between the waist expandable-and-shrinkable member 611 and the absorbent body 604 on the back side of the wearer. When such a level difference ST0 is formed, it reduces the practical compatibility with the body of the wearer and lowers the degree of wear comfort of the absorbent article, and this can result in insufficient absorption of excreted fluid by the portion of the absorbent body 604 on the back side of the wearer.

Methods have been devised to minimize formation of such a level difference ST0, such as using the technology of Patent Literature 2, for example, by overlapping the portion of the absorbent body and the portion of the waist expandable-and-shrinkable member on the back side of the wearer, and bonding together the portion of the absorbent body and the portion of the waist expandable-and-shrinkable member with adhesive. Since the waist expandable-and-shrinkable member and the absorbent body are bonded in this case, the absorbent body can follow movement of the waist expandable-and-shrinkable member. When the waist expandable-and-shrinkable member shrinks, however, the absorbent body also shrinks and deforms in shape, such that the absorption performance is lowered at the absorbent body portion on the back side of the wearer, or the wear comfort can potentially be reduced by formation of wrinkles and the like.

By having the aforementioned configuration shown in FIG. 1, FIGS. 2A and 2B, that employs a waist expandable-and-shrinkable member 11 and a pair of side expandable-and-shrinkable members 7, 7, the absorbent article 1 can have increased compatibility with the body when worn, while also minimizing reduction in absorption performance or reduction in wear comfort of the absorbent body. Specifically, it is as follows.

As shown in FIG. 3B, the waist expandable-and-shrinkable member 11 and the absorbent body 4 are overlapping in the thickness direction T and in contact, and the skin side surface 11p11 of the waist expandable-and-shrinkable member 11 contacts with the absorbent body 4, but it is non-bonded, being not bonded to the absorbent body 4, and therefore it is not adhered with adhesive, for example. Thus, the waist expandable-and-shrinkable member 11 and the absorbent body 4 are mutually non-bonded, and not adhered together with adhesive or the like, and therefore minimally affected by each other's movement. In other words, the waist expandable-and-shrinkable member 11 and the absorbent body 4 can move relative to each other. In this case as well, when the waist expandable-and-shrinkable member 11 shrinks in the widthwise direction W and approaches to come into close contact with the back side BL of the wearer, in order to increase compatibility with the body of the wearer, the portion FP11 of the front sheet 2 corresponding to the waist expandable-and-shrinkable member 11 can be in close contact with the back side BL of the wearer. However, the portion 4B of the absorbent body 4 overlapping and in contact with the waist expandable-and-shrinkable member 11 is virtually unshrunk, and thus the absorbent body 4 undergoes virtually none of the deformation accompanying shrink, thereby making it possible to minimize reduction in absorption performance of the absorbent body 4 and reduction in wear comfort of the absorbent body 4. Also during this time, as the waist expandable-and-shrinkable member 11 positioned on the non-skin side shrinks while the absorbent body 4 positioned on the skin side undergoes virtually no shrink, pressure is exerted by the waist expandable-and-shrinkable member 11 toward the skin side, i.e. toward the absorbent body 4, and the absorbent body 4 can be pressed against the skin side. This allows the portion FP12 of the front sheet 2 corresponding to the absorbent body 4 to also be in close contact with the back side BL of the wearer. As a result, the absorbent body 4 can come into close contact with the wearer, so that the absorption performance can be improved while increasing compatibility with the body when worn.

However, when an absorbent body 4 is pressed against the skin side in this way, mainly the center section in the widthwise direction W of the absorbent body 4 is pressed against the skin side of the wearer, but the edges in the widthwise direction W of the absorbent body 4 can potentially tend to be separated from the skin side. However, since the force of shrink of the pair of side expandable-and-shrinkable members 7, 7 acts on both ends in the widthwise direction W of the laminate of the front sheet 2 and the back sheet 3, the laminate, and particularly the back sheet 3, is pulled by the pair of side expandable-and-shrinkable members 7, 7, whereby the edges in the widthwise direction W of the absorbent body 4 become pressed against the skin side by the back sheet 3 and no longer separate from the skin side. Thus, the function of the waist expandable-and-shrinkable member 11 pressing the absorbent body 4 onto the skin side can apply over the entire widthwise direction W of the absorbent body 4.

Moreover, for this embodiment, each of the pair of side expandable-and-shrinkable members 7, 7 has higher elongation stress per unit length than the waist expandable-and-shrinkable member 11. This allows the waist expandable-and-shrinkable member 11, which has low elongation stress, i.e. easy expansion, to expand before the pair of side expandable-and-shrinkable members 7, 7, thereby allowing the absorbent body 4 to fit better on the skin side.

Figure 4:
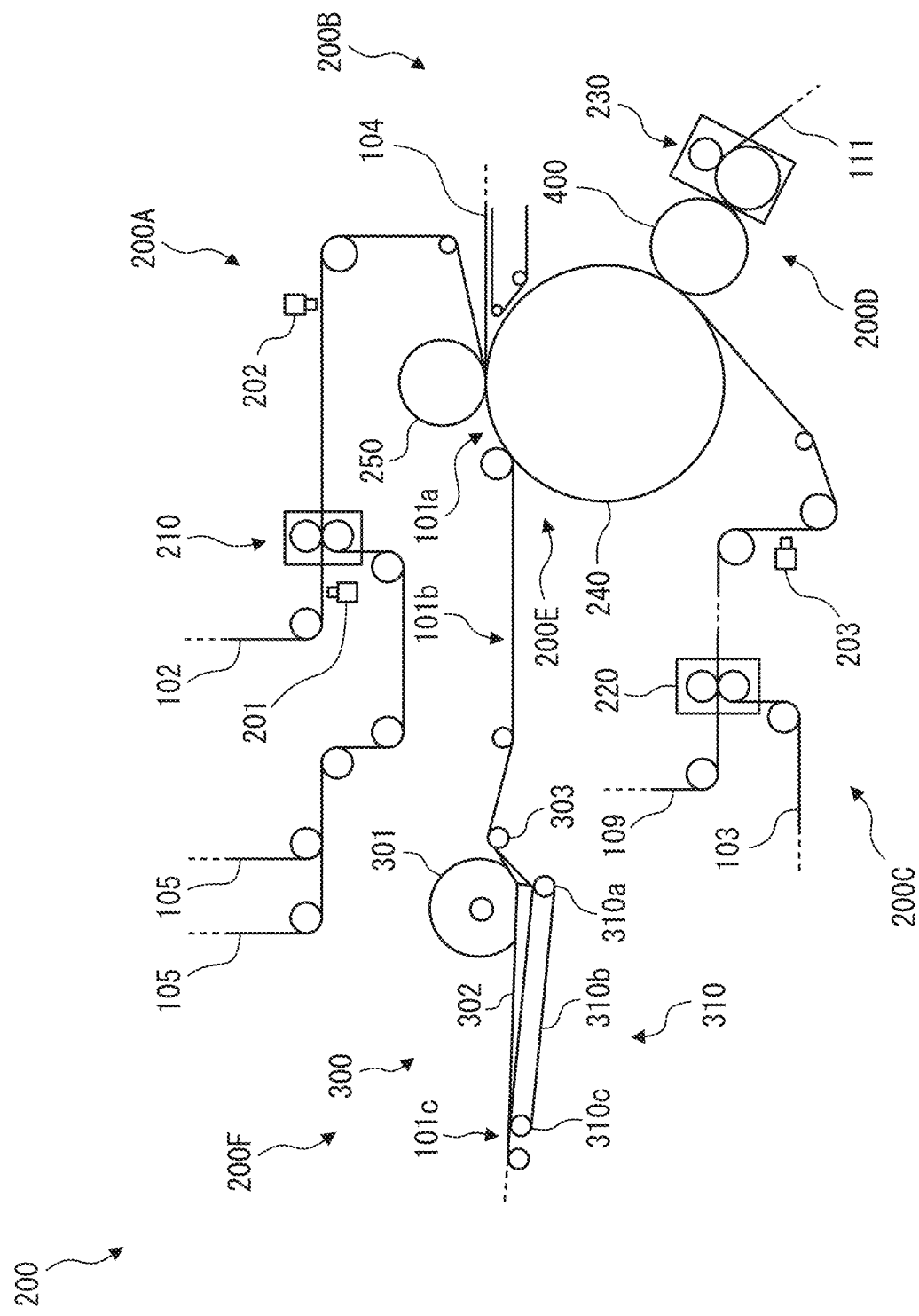
FIG. 4 is a schematic overview of a production apparatus for the absorbent article according to the embodiment.

A method for producing an absorbent article according to this embodiment will now be described. FIG. 4 shows an example of a configuration of a production apparatus 200 for an absorbent article 1. The production apparatus 200 comprises a front sheet-forming unit 200A, an absorbent body-forming unit 200B, a back sheet-forming unit 200C, an expandable-and-shrinkable member-bonding unit 200D, an integral bonding unit 200E and a folding unit 200F. The method for producing an absorbent article using the production apparatus 200 comprises a front sheet-forming step, an absorbent body-forming step, a back sheet-forming step, an expandable-and-shrinkable member bonding step, an integral bonding step, a shrinking step, a pressing step and a folding step.

For transport of the absorbent article 1 and the materials composing it, a machine direction MD, a cross-machine direction CD perpendicular to the machine direction MD along the transport surface, and a thickness direction TD perpendicular to the machine direction MD and the cross-machine direction CD are provided. The lengthwise direction, widthwise direction and thickness direction of the absorbent article 1 and the materials composing it are the same as the machine direction MD, cross-machine direction CD and thickness direction TD, respectively. Thus, for the absorbent article 1 and the materials composing it as well, the machine direction MD, cross-machine direction CD and thickness direction TD are used as the lengthwise direction, widthwise direction and thickness direction, respectively.

In the front sheet-forming step, a continuous front sheet 102 with continuous leak resistant wall sheets 105, 105 bonded is formed by the front sheet-forming unit 200A. That is, the continuous front sheet 102 which is a continuous sheet for the front sheet 2 is transported by a plurality of transport rolls while being coated on one side with adhesive by an adhesive coating applicator 201, and is supplied to a bonding roll 210. Separately, the pair of continuous leak resistant wall sheets 105, 105 as continuous sheets for the pair of leak resistant walls, are transported by a plurality of transport rolls and supplied to the bonding roll 210. At the bonding roll 210, the continuous front sheet 102 and the pair of continuous leak resistant wall sheets 105, 105 are supplied between a pair of bonding rolls that are disposed mutually facing each other. Next, the pair of continuous leak resistant wall sheets 105, 105 are pressed against the side of the continuous front sheet 102 on which the adhesive has been coated, thereby forming a continuous front sheet 102 having the pair of continuous leak resistant wall sheets 105, 105 bonded to both sides in the cross-machine direction CD. Next, the continuous front sheet 102 is transported by a plurality of transport rolls while being coated with adhesive by an adhesive coating applicator 202, on the other side which is the side opposite on which the continuous leak resistant wall sheets 105, 105 have been bonded, and is then supplied to the integral bonding unit 200E (bonding rolls 240, 250).

In the absorbent body-forming step, the absorbent body 104 is formed by an absorbent body-forming apparatus (not shown) in the absorbent body-forming unit 200B. Next, the absorbent body 104 is supplied to the integral bonding unit 200E (bonding rolls 240, 250) by a conveyor belt.

In the back sheet-forming step, a continuous back sheet 103 with a continuous outer sheet 109 bonded is formed by the back sheet-forming unit 200C. That is, the continuous back sheet 103 which is the continuous sheet for the back sheet 3 is transported by a plurality of transport rolls and supplied to a bonding roll 220. Meanwhile, a continuous outer sheet 109 (with the leg expandable-and-shrinkable member 6, side expandable-and-shrinkable members 7, protrusion sections 8 and to-be-bonded member 12 added), which is the continuous sheet for the outer sheet 9, is transported by a plurality of transport rolls while being coated with adhesive on one side by an adhesive coating applicator 203, and supplied to the bonding roll 220. At the bonding roll 220, the continuous outer sheet 109 and the continuous back sheet 103 are supplied between a pair of bonding rolls that are disposed mutually facing each other. Also, the continuous back sheet 103 is pressed against the side of the continuous outer sheet 109 on which the adhesive has been coated to attach them both, thereby forming a continuous back sheet 103 in which the continuous outer sheet 109 is bonded to the back side. Next, the continuous back sheet 103 is transported by a plurality of transport rolls while being coated with adhesive by an adhesive coating applicator 204, on the other side which is the side opposite on which the continuous outer sheet 109 has been bonded, and is then supplied to the integral bonding unit 200E (bonding roll 240).

In the expandable-and-shrinkable member bonding step, the continuous back sheet 103 with the waist expandable-and-shrinkable member 11 attached is formed by the expandable-and-shrinkable member-bonding unit 200D. That is, the continuous expandable-and-shrinkable member sheet 111 which is the continuous sheet for the waist expandable-and-shrinkable member 11 is transported by a plurality of transport rolls while being supplied to a cutting apparatus 230, and the tip sections in the machine direction MD are cut to a prescribed length by the cutter of the cutting apparatus 230. Each cut fragment, i.e. each waist expandable-and-shrinkable member 11, is held at both ends in the cross-machine direction CD by a widening/attaching apparatus 400, and received by the widening/attaching apparatus 400. The waist expandable-and-shrinkable member 11 is rotated approximately 180° while the both ends in the cross-machine direction CD are pulled in the cross-machine direction by the widening/attaching apparatus 400, is pressed against the adhesive-coated surface of the continuous back sheet 103 after the back sheet-forming step on the bonding roll 240 in the expanded state, and is attached to the continuous back sheet 103. In this manner, the continuous back sheet 103 with the waist expandable-and-shrinkable member 11 attached is formed. The continuous back sheet 103 is under tension in the machine direction during this time, and the continuous back sheet 103 undergoes virtually no narrowing even when the waist expandable-and-shrinkable member 11 in the extended and expanded state in the cross-machine direction CD is attached. Next, the continuous back sheet 103 with the waist expandable-and-shrinkable member 11 attached moves over the bonding roll 240 to the integral bonding unit 200E (bonding roll 250), and is supplied to the integral bonding unit 200E (bonding roll 240). During this time, the continuous back sheet 103 has the waist expandable-and-shrinkable member 11 attached to the adhesive-coated side, with no adhesive on the waist expandable-and-shrinkable member 11, the adhesive being coated on the perimeter section of the waist expandable-and-shrinkable member 11.

In the integral bonding step, a semi-processed continuous body 101*a* for the absorbent article comprising the continuous front sheet 102, absorbent body 104 and continuous back sheet 103, is formed by the integral bonding unit 200E. In other words, the continuous front sheet 102 on which the continuous leak resistant wall sheets 105, 105 are bonded and the adhesive is coated is transported from the front sheet-forming step, the absorbent body 104 is transported from the absorbent body-forming step, and the continuous back sheet 103 on which the continuous outer sheet 109 is bonded, the adhesive is coated and the waist expandable-and-shrinkable member 11 is attached is transported from the expandable-and-shrinkable member bonding step, between respective pairs of bonding rolls 240, 250 that are disposed mutually facing each other. Also, the continuous front sheet 102, the absorbent body 104 and the continuous back sheet 103 are sandwiched, compressed and bonded between the pair of bonding rolls 240, 250. The semi-processed continuous body 101*a* of the absorbent article is thus formed comprising the continuous front sheet 102, the absorbent body 104 and the continuous back sheet 103. During this time, in the continuous back sheet 103 on which the waist expandable-and-shrinkable member 11 has been attached, there is no adhesive coated on the waist expandable-and-shrinkable member 11, and therefore no adhesive is present between the waist expandable-and-shrinkable member 11 and the absorbent body 104 and thus the waist expandable-and-shrinkable member 11 and absorbent body 104 are in contact but not bonded. The coating pattern for the adhesive on the front sheet 2 and the coating pattern for the adhesive on the back sheet 3 may be appropriately adjusted by the adhesive coating applicator 202 or adhesive coating applicator 203, for example.

In the shrinking step, the semi-processed continuous body 101*a* separates from the bonding roll 240 and is transported by a plurality of transport rolls while the tension in the machine direction MD is reduced (for example, the rotational speed of the transport rolls is reduced). This allows the waist expandable-and-shrinkable member 11 expanded in the cross-machine direction CD to shrink, thereby allowing the waist expandable-and-shrinkable member 11 to be shrunk in the cross-machine direction CD. In response, the portion of the semi-processed product 1*a* including the waist expandable-and-shrinkable member 11 can also shrink in the cross-machine direction CD. As a result, a semi-processed continuous body 101*b* is formed in which the portions including the waist expandable-and-shrinkable members 11 are shrunk in the cross-machine direction CD.

Next, in the pressing step, the semi-processed continuous body 101*b* with the waist expandable-and-shrinkable member 11 shrunk is supplied to a pressing member 301 and conveying apparatus 310 by a transport roll 303 of the folding unit 200F. Next, the semi-processed continuous body 101*b* is transported in the machine direction MD by the conveying apparatus 310, while the center region of the semi-processed product 1*b* in the cross-machine direction CD is pressed in the direction toward the mounting surface of the semi-processed product 1*b* by the pressing member 301 whose length in the cross-machine direction CD is smaller than the length of the waist expandable-and-shrinkable member 11 in the cross-machine direction CD. As a result, the region of the waist expandable-and-shrinkable member 11 with a plurality of wrinkles becomes pressed.

In the folding step, the semi-processed continuous body 101*b* is transported in the machine direction MD by the conveying apparatus 310, while a pair of side section regions which is on the outer side with respect to the center region of the semi-processed product 1*b* in the cross-machine direction CD are raised by a folding member 302 in the direction opposite from the direction facing the mounting surface of the semi-processed product 1*b* on a pair of folding lines extending along the machine direction MD, and each is folded upward above the center region. A semi-processed continuous body 101*c* is thus formed. The pressing step and the folding step may be carried out in a temporally overlapping manner, or the folding step may be carried out after the pressing step. The semi-processed continuous body 101*c* is then cut into individual absorbent article product portions as the absorbent article 1.

An absorbent article 1 is produced in this manner.

With this absorbent article 1 it is possible to increase compatibility with the body when worn, and to also minimize reduction in absorption performance of the absorbent body and reduction in wear comfort.

With the absorbent article of this embodiment, as a preferred mode, the waist expandable-and-shrinkable member 11 and each of the pair of side expandable-and-shrinkable members 7, 7 are disposed apart from each other. Thus, the portions of the laminate without expansion and shrink between the waist expandable-and-shrinkable member 11 and each of the pair of side expandable-and-shrinkable members 7, 7 can more strongly press the absorbent body 4 against the skin side. Consequently, the absorbent body 4 can come into close contact with the wearer, and the absorption performance can be improved while increasing compatibility with the body when worn.

Furthermore, as a preferred mode for the absorbent article of this embodiment, in the lengthwise direction L, the waist expandable-and-shrinkable member 11 is shifted more toward the backward direction in the lengthwise direction L than the absorbent body 4. Consequently, compared to when the waist expandable-and-shrinkable member 11 is completely overlapping with the absorbent body 4 in the lengthwise direction L, friction and the like between the waist expandable-and-shrinkable member 11 and the absorbent body 4 is reduced and it becomes easier to expand the waist expandable-and-shrinkable member 11 in the widthwise direction W. This allows the waist expandable-and-shrinkable member 11 to apply firmer pressure toward the absorbent body, and to press the absorbent body 4 more to the skin side. This allows the absorbent body 4 to come into close contact with the wearer, so that the absorption performance can be improved while increasing compatibility with the body when worn.

As a preferred mode for the absorbent article of this embodiment, the fastening tape 7a overlaps with the waist expandable-and-shrinkable member 11 in the lengthwise direction L. In this case, the fastening tape 7a overlapping with the waist expandable-and-shrinkable member 11 is the portion of the fastening tape 7a overlapping and bonded to the side expandable-and-shrinkable member 7 in the thickness direction, and it includes the portion thereof having the maximum length in the lengthwise direction L. Also, the entire fastening tape 7a is preferably overlapping with the waist expandable-and-shrinkable member 11 in the lengthwise direction L. In this case, when the pair of side expandable-and-shrinkable members 7, 7 are expanded and the fastening tape 7a of each side expandable-and-shrinkable member 7 has been fastened to the to-be-bonded member 12 (target tape), the force of shrink of the side expandable-and-shrinkable member 7 and the force of shrink of the waist expandable-and-shrinkable member 11 are coordinated between the fastening tape 7a, allowing the absorbent body 4 to be more firmly pressed against the skin side. This allows the absorbent body 4 to come into close contact with the wearer, so that the absorption performance can be improved while increasing compatibility with the body when worn.

As a preferred mode for the absorbent article of this embodiment, the edge 4E2 in the backward direction of the absorbent body 4 is situated between the edge in the frontward direction and the edge in the backward direction of the fastening tape 7a, in the lengthwise direction L. Therefore, the force pulling the fastening tape 7a is exerted on the absorbent body 4 while being exerted on the edge 4E2 of the absorbent body 4, whereby the edge 4E2 of the absorbent body 4 can spread in the widthwise direction W and be pushed against the body, exhibiting an effect of minimizing formation of gaps on dorsal side (leakage prevention).

As a preferred mode for the absorbent article of this embodiment, each of the pair of side expandable-and-shrinkable members 7, 7 overlaps with the absorbent body 4 in the lengthwise direction L, and therefore the force of shrink of each of the pair of side expandable-and-shrinkable members 7, 7 is more easily transmitted to the absorbent body 4 in the laminate, and the absorbent body 4 in the laminate can be more greatly pressed against the skin side. This allows the absorbent body 4 to come into close contact with the wearer, so that the absorption performance can be improved while increasing compatibility with the body when worn.

According to another preferred embodiment of the absorbent article, adhesive is also not provided on the perimeter on the outer side of the region where the waist expandable-and-shrinkable member 11 and the absorbent body 4 overlap as planar view. This allows the waist expandable-and-shrinkable member 11 and the absorbent body 4 to more easily move relative to each other. This can minimize reduction in absorption performance caused by generation of wrinkles 11S or deformation in the absorbent body 4.

The absorbent article according to the present invention is not limited to the embodiments described above and can incorporate appropriate combinations and modifications without departing from a scope of the object and subject matter of the present invention.

The invention claimed is:

1. An absorbent article comprising a front sheet, a back sheet, and an absorbent body disposed in a laminate of the front sheet and the back sheet, and having a lengthwise direction, a widthwise direction and a thickness direction, the absorbent article comprising:
   a waist expandable-and-shrinkable member that is expandable and shrinkable in an expansion-and-shrink direction and disposed between the front sheet and back sheet in the laminate, the expansion-and-shrink direction being along the widthwise direction; and
   a pair of side expandable-and-shrinkable members that are expandable and shrinkable in the expansion-and-shrink direction, the pair of side expandable-and-shrinkable members being formed on a perimeter section of the laminate so that the expansion-and-shrink direction is along the widthwise direction, and one and the other of the pair of side expandable-and-shrinkable members being formed on one edge and the other edge, respectively, in the widthwise direction of the laminate,
   wherein
   the waist expandable-and-shrinkable member
      overlaps with each of the pair of side expandable-and-shrinkable members in the lengthwise direction,
      is disposed on a non-skin side with respect to the absorbent body in the thickness direction, and
      overlaps but non-bonded to the absorbent body in the thickness direction,
   one direction in the lengthwise direction is a frontward direction and the other is a backward direction,
   the waist expandable-and-shrinkable member includes a first edge elongated in the widthwise direction and a second edge elongated in the widthwise direction, and
   an edge of the absorbent body in the backward direction is elongated in the widthwise direction and is situated, in the lengthwise direction, between the first and second edges of the waist expandable-and-shrinkable member.

2. The absorbent article according to claim 1, wherein the waist expandable-and-shrinkable member and each of the pair of side expandable-and-shrinkable members are disposed apart from each other in the widthwise direction.

3. The absorbent article according to claim 1, wherein
   each of the pair of side expandable-and-shrinkable members comprises a fastening tape on an outer side in the widthwise direction, and
   the fastening tape overlaps with the waist expandable-and-shrinkable member in the lengthwise direction.

4. The absorbent article according to claim 1, wherein in the lengthwise direction, each of the pair of side expandable-and-shrinkable members overlaps with the absorbent body.

5. The absorbent article according to claim 1,
   wherein the waist expandable-and-shrinkable member has
      a front end portion overlapping with the absorbent body in the thickness direction, and
      a back end portion not overlapping with the absorbent body in the thickness direction, and overlapping with the front sheet in the thickness direction, and
   wherein the back end portion has
      a first portion located on a perimeter on an outer side of the front end portion, and not bonded to the front sheet, and
      a second portion located on a perimeter on an outer side of the first portion, and bonded to the front sheet.

* * * * *